(12) United States Patent
Ishimaru et al.

(10) Patent No.: US 6,825,016 B1
(45) Date of Patent: Nov. 30, 2004

(54) α-GLYCATED AMINO ACID RELEASING ENZYME (75) Inventors: Kaori Ishimaru, Kyoto (JP); Masayuki Yagi, Kyoto (JP); Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 09/958,515

(22) PCT Filed: Apr. 11, 2000

(86) PCT No.: PCT/JP00/02357

§ 371 (c)(1),
(2), (4) Date: Oct. 9, 2001

(87) PCT Pub. No.: WO00/61732

PCT Pub. Date: Oct. 19, 2000

(30) Foreign Application Priority Data

Apr. 12, 1999 (JP) ............................................. 11-142185

(51) Int. Cl.$^7$ .............................. C12N 9/00; C12N 1/00
(52) U.S. Cl. ...................................... 435/183; 435/243
(58) Field of Search ......................................... 435/183

(56) References Cited

U.S. PATENT DOCUMENTS 5,370,990 A 12/1994 Staniford et al.

FOREIGN PATENT DOCUMENTS

| EP | 0 526 150 | 2/1993 |
|----|-----------|--------|
| EP | 0 678 576 | 10/1995 |
| EP | 1 156 105 | 11/2001 |
| JP | 50-19628  | 7/1975 |
| JP | 63-279782 | 11/1988 |

OTHER PUBLICATIONS

Dees et al., Intern. Journal. of System. Bact., 1985, p. 16–22, 35(1).*

Yabuuchi et al., Intern. Jouranl. System. Bacteriol., 1983, 580–598, 33(3).*

Pau et al., Clin. Chem., 33(3), 377–80, 1987.*

"Isolation, Purification, and Characterization of an Amadori Product Binding Protein from a *Pseudomonas* sp. Soil Strain" C. Gerhardinger, et al., The Journal of Biological Chemistry, vol. 269, No. 44, Nov. 1994, pp. 27297–27302.

F.W.J. Teale "Cleavage of Haem–protein link by acid methylethylhetone" Dep. of Biochemistry, University of Sheffield (Great Britain), vol. 35 p. 543, 1959.

Yoshida et al. "Primary structures of fungal frustosyl amino acid oxidases and their application to the measurement of glycated proteins" Eur. J. Biochem. 242, pp 499–505, 1996.

Kenji Yamamoto "Microbial Endoglycosidases for Analyses of Oligosaccharide Chain in Glycoproteins" J. Biochem. 116, pp 229–235, 1994.

Bisse et al. "High–performance liquid chromatographic separation of human Haemoglobins" Journal of Chromatography, vol. 434, pp 95–110, 1988.

Shin et al., "Identification of the protease producing bacteria to use fish meal wastewater and the producing conditions for the enzyme" Bull. Korean Fish Soc., vol. 22, No. 3, pp 138–146, (abstract only.), 1989.

* cited by examiner

*Primary Examiner*—Michael Meller
(74) *Attorney, Agent, or Firm*—Merchant & Gould P.C.

(57) ABSTRACT

The present invention relates to a novel enzyme (α-GARE) which releases an amino acid residue having a glycated α-amino group (α-GA) from a glycated protein etc. and to bacterial strains producing the same. Examples of the bacterial strains include *Sphingomonas parapaucimobilis* KDK1004 (FERM BP-7041). The α-GARE is contained in the culture supernatant of this strain and α-GA can be released from a glycated peptide by using the same, as shown in FIG. 1.

2 Claims, 8 Drawing Sheets

Lane No. 1    Control FV
Lane No. 2    Controls Leu, Val, His
Lane No. 3    F3P degradation product

Fig. 1

Lane No.1  Control FV
Lane No.2  Controls Leu, Val, His
Lane No.3  F3P degradation product

Fig. 2

Lane No. 1  Control FV
Lane No. 2  Controls Leu, Val, His
Lane No. 3  F2P degradation product
Lane No. 4  F3P degradation product

Fig. 3

Lane No. 1   Control FV
Lane No. 2   Controls Leu, Val, His
Lane No. 3   F 2 P  degradation product
Lane No. 4   F 3 P  degradation product

Fig. 4

Lane No. 1  Control FV
Lane No. 2  Controls Leu, Val, His
Lane No. 3  F 2 P degradation product
Lane No. 4  F 3 P degradation product

α-GLYCATED AMINO ACID RELEASING ENZYME

TECHNICAL FIELD

The present invention relates to a novel enzyme. In particular, the present invention relates to an enzyme which releases an amino acid having a glycated α-amino group.

BACKGROUND ART

Proteases are used in various industrial fields. For example, proteases are used for determining a glycated protein, e.g., glycated albumin, in serum, which can serve as a significant index for the diagnosis, treatment, etc. of diabetes.

Such determination of the glycated protein utilizing the protease can be carried out, for example, by degrading the glycated protein with the protease, reacting the resultant degradation product with a fructosyl amino acid oxidase (hereinafter, referred to as "FAOD"), and then determining oxygen consumption or hydrogen peroxide generation to find the amount of the glycated protein. Examples of the protease include those disclosed in JP 5(1993)-192193 A and JP 7(1995)-289253 A.

The above-mentioned protease pre-treatment of the glycated protein is conducted because FAOD and the like easily act on a glycated amino acid and a glycated peptide whereas they hardly act on the glycated protein itself. Particularly, since the glycated site of glycated hemoglobin (hereinafter, referred to as "HbA1c") is the N-terminal amino acid residue of the β-chain, there has been a demand for a protease capable of treating HbA1c so that FAOD easily can act on this site of the HbA1c.

DISCLOSURE OF THE INVENTION

Therefore, it is an object of the present invention to provide a novel enzyme capable of treating a glycated protein and a glycated peptide so that FAOD easily can act thereon.

First, among various FAODs, the inventors of the present invention have studied the mechanism of the action of the FAOD that acts on a glycated protein, glycated peptide, glycated amino acid, etc. in which a sugar is bound to an α-amino group. From this study, the inventors have found that such FAOD easily acts on the glycated amino acid in which a sugar is bound to an α-amino group whereas it hardly acts on the above glycated protein and glycated peptide. Based on this finding, the inventors have isolated various bacteria from nature, cultured them, and studied the enzymes produced by them. As a result, the inventors have succeeded in isolating the bacteria producing a novel enzyme capable of releasing an amino acid having a glycated α-amino group (α-Glycated Amino acid: hereinafter, referred to as "α-GA") from the glycated protein or glycated peptide in which sugar is bound to an α-amino group (an N-terminal amino group), thereby establishing the present invention. The novel enzyme (α-Glycated Amino acid Releasing Enzyme: hereinafter, referred to as "α-GARE") according to the present invention can release α-GA, for example, from the above glycated protein or glycated peptide. Hence, the determination of HbA1c using the FAOD that easily acts on α-GA can be made practical in clinical tests etc. by the use of this novel enzyme. The novel enzyme according to the present invention can be utilized not only for the determination of HbA1c but also in various application fields, e.g., for the determination of other glycated proteins. Furthermore, in addition to the catalytic functions of releasing α-GA, α-GARE of the invention may have other catalytic functions, e.g., the function of cleaving other peptide bonds. Examples of the novel bacterial strains isolated by the present inventors include bacterial strains of the genus *Sphingobacterium*, the genus *Sphingomonas*, the genus *Comamonas*, the genus *Mucor*, and the genus *Penicillium*. However, it is to be noted that α-GARE according to the present invention is not limited to those derived from the strains of these genera.

The glycated amino acid released by α-GARE is not specifically limited as long as it has a glycated α-amino group. However, since the N-terminal valine residue is glycated in HbA1c as described above, the glycated amino acid released by α-GARE preferably is a glycated valine (hereinafter, referred to as "α-GV").

Examples of α-GARE according to the present invention include the following five types.

The first α-GARE is derived from the bacterial strain of the genus *Sphingobacterium* and most preferably from *Sphingobacterium mizutae* KDK1003. *Sphingobacterium mizutae* KDK1003 was isolated from the soil novelly by the present inventors. *Sphingobacterium mizutae* KDK1003 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17348 since Mar. 29, 1999. Bacteriological properties of this strain are as shown below.

(Morphological Characteristics)

This strain is a non-motile, rod-shaped bacterium (bacillus) of 0.5×1.2 μm.

(Culture Characteristics)

When cultured in an agar medium according to the usual method, the strain forms a colony that is circular in form, low convex in elevation, with an entire margin. The colony color is yellow.

(Physiological Characteristics)

| | |
|---|---|
| Gram's stain: | negative |
| Oxygen requirement: | facultative anaerobic |
| Nitrate reduction: | – |
| Indole production: | – |
| Glucose acidification: | – |
| Arginine dihydrolase: | – |
| Urease: | – |
| Esculin hydrolysis: | – |
| Gelatin hydrolysis: | – |
| β-galactosidase: | – |
| Substrate utilization | |
| Glucose: | + |
| L-arabinose: | + |
| D-mannose: | + |
| D-mannitol: | – |
| N-acetyl-D-gluconsamine: | – |
| Maltose: | + |
| Potassium gluconate: | – |
| n-capric acid: | – |
| Adipic acid: | – |
| DL-malic acid: | – |
| Sodium citrate: | – |
| Phenyl acetate: | – |

The second α-GARE is derived from the bacterial strain of the genus *Sphingnomonas* and most preferably from *Sphingomonas parapaucimobilis* KDK1004. *Sphingomonas*

*parapaucimobilis* KDK1004 also was isolated from the soil novelly by the present inventors. *Sphingomonas parapaucimobilis* KDK1004 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17347 since Mar. 29, 1999. The original deposit has been transferred to one under the Budapest Treaty under the Accession Number FERM BP-7041 (Date of acceptance: Feb. 21, 2000) in the National Institute of Bioscience and Human Technology as an international depositary authority. Bacteriological properties of this strain are as shown below.

(Morphological Characteristics)

This strain is a motile, rod-shaped bacterium (bacillus) of 0.8×2.0 μm.

(Culture Characteristics)

When cultured in an agar medium according to the usual method, the strain forms a colony that is circular in form, low convex in elevation, with an entire margin. The colony initially is translucent and then turns to light yellow. When cultured in the Mac Conkey's culture medium, the strain does not grow. Further, at a culture temperature of 42° C., the strain grows, albeit weakly.

(Physiological Characteristics)

| | |
|---|---|
| Gram's stain: | negative |
| Oxygen requirement: | facultative anaerobic |
| Nitrate reduction: | – |
| Indole production: | – |
| Glucose acidification: | – |
| Arginine dihydrolase: | – |
| Urease: | – |
| Esculin hydrolysis: | + |
| Gelatin hydrolysis: | – |
| β-galactosidase: | + |
| Gas generation from glucose: | – |
| Substrate utilization | |
| Glucose: | + |
| L-arabinose: | + |
| D-mannose: | – |
| D-mannitol: | + |
| N-acetyl-D-gluconsamine: | + |
| Maltose: | + |
| Potassium gluconate: | – |
| n-capric acid: | – |
| Adipic acid: | – |
| DL-malic acid: | – |
| Sodium citrate: | – |
| Phenyl acetate: | + |

The third α-GARE is derived from the bacterial strain of the genus *Comamonas* and most preferably from *Comamonas acidovorans* KDK1005. *Comamonas acidovorans* KDK1005 also was isolated from the soil novelly by the present inventors. *Comamonas acidovorans* KDK1005 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17346 since Mar. 29, 1999. Bacteriological properties of this strain are as shown below.

(Morphological Characteristics)

This strain is a motile, rod-shaped bacterium (bacillus) of 0.6×1.5 μm.

(Culture Characteristics)

When cultured in an agar medium according to the usual method, the strain forms a colony that is circular in form, convex in elevation, with rhizoids. The colony color is shiny yellow.

(Physiological Characteristics)

| | |
|---|---|
| Gram's stain: | negative |
| Oxygen requirement: | aerobic |
| Nitrate reduction: | – |
| Indole production: | – |
| Glucose acidification: | – |
| Arginine dihydrolase: | – |
| Urease: | – |
| Esculin hydrolysis: | – |
| Gelatin hydrolysis: | – |
| β-galactosidase: | – |
| Substrate utilization | |
| Glucose: | – |
| L-arabinose: | + |
| D-mannose: | – |
| D-mannitol: | + |
| N-acetyl-D-gluconsamine: | – |
| Maltose: | – |
| Potassium gluconate: | + |
| n-capric acid: | + |
| Adipic acid: | – |
| DL-malic acid: | + |
| Sodium citrate: | – |
| Phenyl acetate: | – |

The fourth α-GARE is derived from the bacterial strain of the genus *Mucor* and most preferably from *Mucor circinelloides f. janssenii* KDK3004. *Mucor circinelloides f. janssenii* KDK3004 also was isolated from the soil novelly by the present inventors. *Mucor circinelloides f. janssenii* KDK3004 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17345 since Mar. 29, 1999. Bacteriological properties of this strain are as shown below.

(Morphological Characteristics)

This strain forms subglobose sporangiospores of 4 to 6 μm diameter. The sporangia are black and about 70 μm in diameter, and collarettes are observed at the substrate thereof. The width of each hypha is 10 to 12 μm. No rhizoid is formed.

(Culture Characteristics)

When cultured in an agar medium according to the usual method, the strain forms zygospores only by the gametangial copulation. The aerial hyphae with a cotton-wool-like shape initially are white and turn gray gradually. The rear face of the colony is white. The strain does not grow well at 37° C. and does not grow at all at 40° C.

The fifth α-GARE is derived from the bacterial strain of the genus *Penicillium* and most preferably from *Penicillium waksmanii* KDK3005. *Penicillium waksmanii* KDK3005 also was isolated from the soil novelly by the present inventors. *Penicillium waksmanii* KDK3005 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17344 since Mar. 29, 1999. Bacteriological properties of this strain are as shown below.

(Morphological Characteristics)

Conidiophores rising from the substrate are smooth and covered with thin cell walls and form no terminal vesicle.

The conidiophores do not branch. Two to five metulae forming verticils are developed. A single phialide of 0.9 μm is formed at the tip of each metula. The shape of the phialide is like a flask having a tapered short neck. The conidiophores form catenulate, substantially spherical conidiophores of 3 μm diameter, which are covered with smooth cell walls.

(Culture Characteristics)

When cultured in an agar medium according to the usual method, the strain forms a colony that becomes 30 mm in diameter by the culture peroformed at 25° C. for 7 days. The colony has a felt-like green surface. The hyphae exhibit no color. The rear face of the colony is light blue. The strain produces no leachate. Growth is negative when cultured at 37° C.

A method of determining a glycated protein or a glycated peptide according to the present invention includes: degrading a glycated protein or a glycated peptide with an enzyme; causing a redox reaction between the resultant degradation product and FAOD; and determining the redox reaction so as to determine the glycated protein or the glycated peptide. In this method, the novel enzyme (α-GARE) according to the present invention is used as the above enzyme. The type of the α-GARE used in this method is decided appropriately depending on the type, concentration, etc. of the glycated protein or glycated peptide to be determined. The α-GARE may be used alone or in combination of two or more types. The glycated protein or the like may be degraded by the pretreatment with another enzyme (e.g., protease) so that the α-GARE more easily can act thereon.

In the determination method according to the present invention, the redox reaction preferably is determined by measuring the amount of hydrogen peroxide produced by the redox reaction or the amount of oxygen consumed by the redox reaction. The amount of the hydrogen peroxide preferably is measured using a peroxidase and a substrate that develops color by oxidation (hereinafter, referred to as "chromogenic substrate"). The amount of the hydrogen peroxide can be determined not only by the above-mentioned enzymic method utilizing the peroxidase or the like but also by an electrical method, for example.

Examples of the chromogenic substrate include N-(carboxymethylaminocarbonyl)-4,4'-bis(dimethylamino) diphenylamine sodium (for example, the trade name "DA-64" available from Wako Pure Chemical Industries, Ltd.), orthophenylenediamine (OPD), and a substrate obtained by combining a Trinder's reagent and 4-aminoantipyrine. Examples of the above Trinder's reagent include phenols, phenol derivatives, aniline derivatives, naphthols, naphthol derivatives, and naphthylamine, naphthylamine derivatives. Further, in place of the above aminoantipyrine, it is possible to use aminoantipyrine derivatives, vanillin diamine sulfonic acid, methyl benzothiazolinone hydrazone (MBTH), sulfonated methyl benzothiazolinone hydrazone (SMBTH), and the like. Among these chromogenic substrates, N-(carboxymethylaminocarbonyl)-4,4'-bis(dimethylamino) diphenylamine sodium is particularly preferable.

In the determination method according to the present invention, a sample to be analyzed preferably is blood cells because determining HbA1c in blood cells is useful for diagnosis of diabetes as described above. However, the sample is not limited to the blood cells because blood components other than the blood cells (whole blood, plasma, serum, etc.); biological samples such as urine and spinal fluid; beverage such as juice; food such as soy sauce and sauce, etc. also contain glycated proteins. Also, an analyte to be determined is not limited to HbA1c and can be, for example, a glycated protein such as gelatin and casein or a glycated peptide.

A kit for determining a glycated protein or a glycated peptide according to the present invention includes a protease, FAOD, a peroxidase, and a substrate that is oxidized through a reaction with the peroxidase. In this determination kit, the protease contains an α-GARE of the present invention. The determination method according to the present invention can be carried out rapidly and easily by using this kit. Also in this determination kit, the α-GARE may be used alone or in combination of two or more types.

In the determination kit according to the present invention, as the substrate to be oxidized, the chromogenic substrates described above preferably are used. Further, an analyte and a sample to be used in this kit also are as described above.

A method of producing α-GARE of the invention includes the step of culturing a novel bacterial strain of the invention. This method enables easy production of α-GARE according to the present invention.

It is preferable that the method of producing α-GARE of the present invention further includes the following purification steps (a) to (c):

(a) the step of removing the bacterial cells from the culture solution to prepare a supernatant;

(b) the step of precipitating the protein contained in the supernatant with ethanol; and (c) the step of separating the protein by chromatography.

The above purification steps are not specifically limited and may be performed along with other purification steps. Further, it is possible to perform, for example, the step (a) only; to perform the two or more steps; or to perform the same step repeatedly.

The α-GARE of the invention obtained through the above-mentioned culture of the bacterial strain may be used in the state of being contained in the culture solution or in the state of being purified. The α-GARE can be used regardless of its purification level as long as it can release α-GA from the glycated protein or the like. However, if purified, a specific activity of the α-GARE can be improved because the components other than the α-GARE in the culture solution are removed by the purification. Accordingly, the amount of the α-GARE to be used can be reduced, which facilitates the handling of the α-GARE. In addition, when the α-GARE is used for causing various reactions, influence given by the components other than the α-GARE can be avoided.

The genes encoding α-GARE of the present invention preferably are prepared by determining the amino acid sequence and the gene sequence of the α-GARE purified through the above purification steps. The genes encoding α-GARE of the invention are not limited to those necessary for the expression of the α-GARE. Examples of such genes include a DNA fragment, RNA, etc., which are used as a probe or primer, and a fragment synthesized chemically based on the gene sequence of the above α-GARE. Using such genes, a recombinant or the like may be prepared to produce α-GARE. The genes of α-GARE according to the present invention can be obtained, for example, in the following manner.

First, α-GARE of the invention is purified, for example, by the purification steps described below. Then, the amino acid sequence thereof is determined by the usual method such as Edman degradation, from which the gene sequence of the α-GARE is assumed. Then, based on the gene sequence thus obtained, a DNA fragment, RNA fragment, or the like is produced by the usual method such as chemical synthesis or the like. Then, the genes of the α-GARE of the invention can be obtained by cloning the genes encoding the α-GARE from a novel bacterial strain of the invention using the DNA fragment, RNA fragment, or the like as a primer, probe, or the like.

BEST MODE FOR CARRYING OUT THE INVENTION

Screening of a bacterial strain producing α-GARE according to the present invention can be carried out, for example, by culturing the bacterial strain in the soil according to an isolation culture method, inducing a degradation reaction of a glycated peptide by the resultant culture solution, and then analyzing the resultant degradation product by thin layer chromatography (TLC), as specifically described below. The inventors of the present invention have conducted an elaborate study on how to isolate the bacterial strain producing the α-GARE and finally established the following screening method. It can be asserted with good reason that success in isolating the bacterial strain producing the α-GARE of the invention is attributed to the establishment of this screening method.

(1) Culture Method

The liquid nutrient medium shown below is sterilized at 121° C. for 20 minutes in an autoclave. A soil sample is suspended in sterilized water, which is then added to the above-mentioned sterilized liquid nutrient medium, which is then cultured by a shake culture (111 rpm) at 30° C. for 48 hours. The culture solution thus obtained is centrifuged (12,000 G, 15 min, 4° C.) and the supernatant is collected.

| (Liquid Nutrient Medium) | |
|---|---|
| Malt extract (the trade name "Malt extract", Difco Laboratories) | 2.0 g |
| D-glucose (Nacalai Tesque, Inc.) | 2.0 g |
| Peptone (the trade name "Becto peptone", Difco Laboratories) | 0.1 g |
| Distilled water | 100 ml |

(2) Degradation Reaction of Glycated Peptide
(Method of Producing Glycated Peptide and Glycated Amino Acid)

Using valine, glucose, and each peptide shown below, a glycated peptide with a glycated α-amino group having the amino acid sequence that is identical to the N-terminal amino acid sequence of the β-chain of HbA1c and α-fructosyl valine (Hereinafter, referred to as "FV") are produced according to the usual method.

(Peptide)

Val-His (Peptide Institute Inc.: The glycation product thereof hereinafter is referred to as "F2P".)

Val-His-Leu (Peptide Institute Inc.: The glycation product thereof hereinafter is referred to as "F3P".)

Val-His-Leu-Thr (Biolink Corporation: The glycation product thereof hereinafter is referred to as "F4P".)

Val-His-Leu-Thr-Pro (Sigma Chemical Co.: The glycation product thereof hereinafter is referred to as "F5P".)

Val-His-Leu-Thr-Pro-Glu-Glu-Lys-Ser (Biolink Corporation: The glycation product thereof hereinafter is referred to as "F9P".)

(L-Amino Acid)

Val, Leu, and His (Wako Pure Chemical Industries, Ltd.)

(Degradation Method)

The above glycated peptides respectively are dissolved in distilled water so as to give a concentration of 0.01 mol/l to prepare glycated peptide aqueous solutions. Subsequently, 50 μl of the glycated peptide aqueous solutions respectively are mixed with 100 μl of the above culture supernatant, and the resultant mixtures are reacted at 37° C. overnight. The reaction solutions thus obtained are then lyophilized.

(3) TLC Analysis

The degradation products of the above glycated peptides are analyzed by TLC for the presence of α-GA released from the above glycated peptides to examine the presence or absence of an α-GARE activity. The reagent to be used and the method of conducting the analysis are described in the following.

(Thin Layer Plate)

Trade name "Pre-Coated TLC plate SILICA GEL 60" (Merck & Co,. Inc.)

(Detection Reagent)

Ninhydrin (Funakoshi Co., Ltd.) is dissolved in 75 vol. % ethanol so as to give a concentration of 0.5 vol. %.

(Development Solvent)

Butanol (Nacalai Tesque, Inc.), an acetic acid (Nacalai Tesque, Inc.), and distilled water are mixed with each other in the volume ratio of 2:1:1.

(Method of Conducting Analysis)

The above thin layer plate previously is prepared so as to have a solvent developing distance of 8 cm and a starting line of a sample spot is set at 1 cm from the bottom of the thin layer plate. Just before starting TLC analysis, the above-mentioned lyophilized reaction solutions respectively are dissolved in 15 μl of 50 vol. % ethanol, which are then spotted on the starting line with a 25 μl syringe. As controls, the above-mentioned FV and respective amino acids also are spotted on the starting line in the same manner. Then, the thin layer plate is placed in a development chamber that previously has been saturated with the above-mentioned developing solvent until the development solvent rises up to a distance of about 8 cm from the starting line. The development solvent should be filled in the development chamber in such a manner that the plate is immersed in the solvent up to distance of about 0.5 cm from the bottom.

After the development, the thin layer plate completely is air-dried in a draft, onto which the above detection reagent (ninhydrin solution) is sprayed. Then, the plate is heated with a preheated hot stirrer (100° C.) to conduct a coloring test. In this coloring test, the sample exhibiting the same mobility as that of the control FV is determined as α-GARE activity positive. The bacterial stain of the culture solution used for preparing the α-GARE-activity-positive sample is the strain producing α-GARE.

The TLC analysis is not limited to the above-mentioned ninhydrin detection and can be, for example, a fluorescence detection using another reagent such as fluorescamine and ethylenediamine sulfate.

Further, as the above controls, for example, α-GA of a glycated protein or glycated peptide serving as a substrate preferably is used.

Examples of novel bacterial strains isolated by the present inventors with this screening method include the above-mentioned *Sphingobacterium mizutae* KDK1003 (FERM P-17348), *Sphingomonas parapaucimobilis* KDK1004 (FERM BP-7041), *Comamonas acidovorans* KDK1005 (FERM P-17346), *Mucor circinelloides f. janssenii* KDK3004 (FERM P-17345), and *Penicillium waksmanii* KDK3005 (FERM P-17344).

The substrate usable for the detection of α-GARE according to the present invention and for the determination of an α-GARE activity is not limited to the above-mentioned glycated peptides etc. Examples of the substrate include a glycated protein, glycated peptide, and the like having a glycated N-terminal α-amino group. In the case where such glycated protein, glycated peptide, and the like are used as a substrate, α-GARE can be detected/determined, for example, by causing a redox reaction (e.g., color development reaction) of the released α-GA using the FAOD described later.

Examples of the above glycated protein include HbA1c and glycated globin. These glycated proteins may be those occurring naturally or those synthesized by Amadori rearrangement between sugars and proteins. The glycated globin can be prepared by the globinization of the HbA1c that has been purified using HPLC etc., according to the method proposed by Teale (Teale, F. W. J, Biochem, Biophys, Acta, 35, 543, 1959). When glycating various proteins by synthesis, sugars to be used are not specifically limited. Examples of the sugars include aldose, e.g. glucose, and ketose.

The above glycated peptide can be prepared, for example, by degrading the above-mentioned glycated protein with a protease. Alternatively, the above glycated peptide can be synthesized by the Amadori rearrangement between sugar and a synthetic peptide. The length of the glycated peptides is not specifically limited. However, the number of amino acid residues is in the range of 2 to 20 and preferably in the range of 2 to 8, for example.

As the peptide used in the Amadori rearrangement with sugar, a natural peptide and synthetic peptide can be used, for example. The amino acid composition of these peptides is not specifically limited. However, the peptide containing no arginine or lysine preferably is used. If the peptide containing no arginine or lysine are glycated, only an α-amino group thereof is glycated to give a glycated peptide. Accordingly, by using such glycated peptide, only an α-GARE activity can be detected.

Specifically, in the case where α-GARE is used for the determination of HbA1c, the above glycated peptides preferably have the amino acid sequence that is identical to the N-terminal amino acid sequence of the β-chain of HbA1c. The glycated peptide in which the α-amino group of N-terminal Val is glycated as described in "Degradation Reaction of Glycated Peptide" above is an example of such glycated peptide. Further, by degrading HbA1c with trypsin for example, a glycated peptide with eight amino acid residues in which the α-amino group of the N-terminal Valine, is glycated can be obtained.

Further, in the case where the glycated peptide and the like having a glycated N-terminal α-amino group are used as a substrate for α-GARE, the α-GARE can be detected/determined not only by detecting the released α-GA but also by detecting the remaining peptide after the α-GA has been released.

Such glycated peptide is not specifically limited and can be, for example, dipeptides such as FV-Leu (hereinafter, "FVL"), FV-Gln (hereinafter, "FVQ"), FV-Ala (hereinafter, "FVA"), and FV-Asn (hereinafter, "FVN"). FV is released from these dipeptides by the α-GARE, thereby generating Leu, Gln, Ala, and Asn, respectively. The α-GARE can be detected by reacting Leu with leucine dehydrogenase; Gln with glutamate dehydrogenase; Ala with alanine amine transferase, α-ketoglutaric acid, and lactate dehydrogenase; Ans with asparagine aminotransferase, α-ketoglutaric acid, malate dehydrogenase, etc., and then determining NADH generation or NAD generation by measuring the absorbance (at the wavelength of 340 nm).

Further, examples of a glycated tripeptide include FV-Leu-Ser (hereinafter, "FVLS"). FV is released from FVLS by α-GARE, thereby generating Leu-Ser. The Leu-Ser is degraded by hydrolase such as aminopeptidase, chymotrypsin, or proteinase K to give leucine, and the leucine thus generated can be determined in the same manner as above. The length of the peptide is not specifically limited.

Further, as a substrate for α-GARE, it is also possible to use a substrate including an amino acid and a detection group, in which the amino acid has a glycated α-amino group; the detection group is bound to an α-carboxyl group of the amino acid by an amide linkage or ester linkage, and the detection group cannot be detected in its binding state whereas it can be detected if released.

α-GARE cleaves the amide linkage or ester linkage between α-GA and the detection group upon reacting with the above-mentioned substrate, thereby releasing the α-GA and the detection group. The detection group released due to this cleavage develops color/fluorescence for example, thus enabling the detection/determination of the α-GARE.

The above detection group is not specifically limited, and a detection group that can be detected by color or fluorescence it develops as described, above preferably is used, for example. Examples of the detection group that can be detected by color include paranitroanilide (hereinafter, referred to as "p-NA"), para-nitrophenol, indole, β-naphthylamide, and 4-methoxy-β-naphthylamide (4MβNA). Further, examples of the detection group that can be detected by fluorescence include 4-methyl-coumaryl-7-amide. Specifically, when p-NA or paranitrophenol is used, the absorbance around the wavelength of 405 to 410 nm, for example, is measured with a spectrophotometer etc. On the other hand, when 4methyl-coumaryl-7-amide is used, the absorbance around the wavelength of 460 nm, for example, is measured after being excited at the wavelength of 380 nm.

The reason why the α-GARE can release the α-GA regardless of whether the detection group is bound to the α-carboxyl group by the amide linkage or ester linkage is conceived that the α-GARE recognizes the glycated site of the α-amino group to release the α-GA.

The above-mentioned substrate for α-GARE including the detection group bound to the α-carboxyl group can be prepared, for example, using a commercially available amino acid with a detection group bound thereto and a sugar, according to the usual method.

α-GARE of the invention can be produced by culturing an α-GARE-producing bacterial strain of the invention, for example, according to a method equivalent to the above-mentioned culture method. The culture conditions of *Sphingobacterium mizutae* KDK1003 (FERM P-17348) are, for example, the culture temperature in the range of 20° C. to 37° C., the culture time in the range of 12 to 120 hours, and the culture medium pH in the range of 6.0 to 9.5. The culture conditions of *Sphingomonas parapaucimobilis* KDK1004 (FERM BP-7041) are, for example, the culture temperature in the range of 20° C. to 37° C., the culture time in the range of 12 to 120 hours, and the culture medium pH in the range of 6.0 to 9.5. The culture conditions of *Comamonas acidovorans* KDK1005 (FERM P-17346), *Mucor circinelloides f. janssenii* KDK3004 (FERM P-17345), and *Penicillium waksmanii* KDK3005 (FERM P-17344) are, for example, the culture temperature in the range of 20° C. to 37° C., the culture time in the range of 12 to 120 hours, and the culture medium pH in the range of 5.0 to 9.0.

Further, by separating and purifying the α-GARE in the culture solution according to the usual method, an enzyme preparation of the α-GARE can be obtained. The purification of the α-GARE can be achieved by combining known methods such as salting-out with ammonium sulfate or the like, isoelectric precipitation, ethanol precipitation, ion-exchange chromatography, gel chromatography, affinity chromatography, hydrophobic chromatography, etc. The following is an example of a method of purifying α-GARE derived from *Sphingobacterium mizutae* KDK1003 (FERM P-17348).

First, the above-mentioned culture solution is centrifuged (12,000 G, 15 min, 4° C.) to remove the bacterial cells and the supernatant is obtained. Then, the supernatant is concentrated 40-fold (by volume) using an ultrafiltration membrane (3 kDa molecular weight cut off: the trade name "MICROZA" available from Asahi Chemical Industry Co., Ltd.). To this concentrated solution is added one third its volume of an anion exchange resin (the trade name "DEAE Sepharose FF" available from Pharmacia Corporation) to attach and elute the α-GARE according to the batch method. First, the concentrated solution is washed with 10 mmol/l dibasic potassium phosphate aqueous solution and then with 10 mmol/l dibasic potassium phosphate aqueous solution containing 0.05 mol/l NaCl to remove non-attached proteins. After that, the α-GARE is eluted with 10 mmol/l dibasic potassium phosphate aqueous solution containing 0.15 mol/l NaCl to collect α-GARE active fractions.

Next, the active fractions are applied to an anion exchange resin column (the trade name "Q-Sepharose FF" available from Pharmacia Corporation) that has been equilibrated with 20 mmol/l potassium phosphate buffer (pH 7.5) to attach the α-GARE, and then are washed with the above buffer. Then, using 20 mmol/l potassium phosphate buffer containing NaCl (pH 7.5), the α-GARE is eluted according to the stepwise method performed at a NaCl concentration in the range of 0.2 mol/l to 0.26 mol/l. In this case, the α-GARE is eluted with 20 mmol/l potassium phosphate buffer containing 0.26 mol/l NaCl.

In this manner, a partially purified enzyme solution of the α-GARE according to the present invention can be obtained. It is to be noted that α-GAREs derived from other novel bacterial strains of the invention can be purified in the same manner.

Further, the culture medium used for culturing the novel bacterial strains according to the present invention is not limited to the above-mentioned liquid nutrient medium. For example, the hemoglobin (Hb) culture medium show below also can be used. Further, the Hb solution contained in this Hb medium can be prepared in the manner described below.

| (Hb Culture Medium: pH 6.0) | |
|---|---|
| Hb solution | 0.2 wt. % |
| $K_2HPO_4$ | 0.2 wt. % |
| $MgSO_4 \cdot 7H_2O$ | 0.02 wt. % |
| Trace metal salt solution | 1.0 wt. % |
| Trace vitamin solution | 0.2 wt. % |

(Hb Solution)

Fresh blood is centrifuged (2,000 G, 10 min, room temperature) and the red blood cells are collected. The equivalent amount (volume) of distilled water is added to the red blood cells to induce hemolysis. The resultant hemolysate is then centrifuged (2,000 G, 15 min, room temperature) to remove red cell membranes etc. The solution thus obtained is used as the Hb solution.

| (Trace Metal Salt Solution) | |
|---|---|
| $CaCl_2 \cdot 2H_2O$ | 200 mg |
| $H_3BO_3$ | 50 mg |
| $CuSO_4 \cdot 5H_2O$ | 20 mg |
| KI | 50 mg |
| $FeSO_4 \cdot 7H_2O$ | 100 mg |
| $MnSO_4 \cdot 5H_2O$ | 200 mg |
| $ZnSO_4 \cdot 7H_2O$ | 200 mg |
| $Na_2MoO_4 \cdot 2H_2O$ | 50 mg |
| Residue | water (the total volume = 500 ml) |
| (Trace Vitamin Solution) | |
| Ca-pantothenic acid | 40 mg |
| Inositol | 20 mg |
| Niacin | 40 mg |
| ρ-aminobenzoate | 20 mg |
| Pyridoxine hydrochloride | 40 mg |
| Thiamine hydrochloride | 40 mg. |
| Biotin | 0.2 mg |
| Vitamin $B_{12}$ | 0.05 mg |
| Residue | water (the total volume = 100 ml) |

Next, a method of determining a glycated protein or a glycated peptide according to the present invention will be explained by taking as an example the case where a sample is blood cells and the glycated protein (e.g., HbA1c) contained therein are determined using α-GARE and FAOD.

First, blood cell fractions are separated from the whole blood according to the usual method such as centrifugal separation and hemolysis of the blood cell fractions is induced. The method of inducing the hemolysis is not specifically limited. Examples of the method include a method using a surfactant, a method using ultrasonic waves, and a method utilizing the difference in osmotic pressure. Among these, the method using a surfactant is preferable on account of the ease of operation.

Examples of the surfactant include polyoxyethylene-p-t-octylpbenyl ethers such as, for example, the trade name "Triton X-100"; polyoxyethylene sorbitan alkyl esters such as, for example, the trade name "Tween-20"; and poly (oxyethylene) alkyl ethers such as, for example, the trade name "Brij 35". The treatment with the above surfactant can be carried out under the following conditions: for example, in the case where the solution to be treated contains 1 to 10 vol. % of blood cells, the surfactant is added to the solution so as to give a concentration of 0.1 to 1 wt. % and the resultant mixture is stirred at room temperature for about 5 seconds to 1 minute.

Subsequently, the above-mentioned sample hemolysate is enzyme-treated with the α-GARE of the invention, thereby releasing α-GA from the glycated protein in the sample hemolysate. The above-mentioned enzyme treatment with the α-GARE is conducted, for example, in buffer. The treatment conditions are decided appropriately depending on, for example, the type (e.g., difference in derivation or the like) of the α-GARE to be used and the types and concentration of the glycated protein or glycated peptide.

For example, in the case where the analyte is HbA1c and the α-GARE derived from *Sphingomonas parapaucimobilis* KDK1004 (FERM BP-7041) is used, the enzyme treatment is conducted, for example, under the following conditions: the α-GARE concentration of the reaction solution in the range of 0.01 U/l to 1 KU/l, the temperature in the range of 15° C. to 60° C., the reaction time in the range of 3 minutes to 6 hours, and the pH in the range of 5.0 to 10.0; preferably, the temperature in the range of 30° C. to 37° C., the reaction time in the range of 5 to 60 minutes, and the pH in the range of 6 to 8. In this case, Tris hydrochloric acid (HCl) buffer, phosphate buffer, Good's buffer (EPPS buffer, PIPES buffer, etc.), and the like can be used as the above buffer. Also, α-GARE derived from other novel bacterial strains of the invention can be used in the same manner.

Next, the degradation product (α-GA) obtained through the above-mentioned α-GARE treatment is treated with FAOD. The degradation reaction of the α-GA catalyzed by FAOD is represented by Formula (1) below.

(Formula 1)

As shown in Formula (1), if the degradation product (α-GA: $R^1$—CO—CH$_2$—NH—$R^2$) obtained through the α-GARE treatment is treated with FAOD, a sugar ($R^1$—CO—CHO), an amino acid (NH$_2$—$R^2$), and hydrogen peroxide (H$_2$O$_2$) are generated.

In Formula (1), $R^1$ denotes a residue derived from a sugar that is not yet subjected to the glycation reaction (i.e., sugar moiety). The sugar moiety ($R^1$) is an aldose residue when the unreacted sugar is aldose, and a ketose residue when the unreacted sugar is ketose. When the unreacted sugar is glucose, for example, the sugar in the glycated product takes on the fructose structure after the glycation reaction due to Amadori rearrangement. In this case, the sugar moiety ($R^1$) is a glucose residue (aldose residue). This sugar moiety ($R^1$) can be represented, for example, by —[CH(OH)]$_n$—CH$_2$OH where n denotes an integer of 0 to 6.

Further, in Formula (1), $R^2$ denotes an amino acid residue having a glycated α-amino group and $R^2$ can be represented by Formula (2) below. In Formula (2), $R^3$ denotes an amino-acid side chain group.

(Formula 2)

The above FAOD is not specifically limited as long as it catalyzes the above-mentioned degradation reaction and may have other catalytic functions, for example. Similarly to the enzyme treatment with α-GARE, the FAOD treatment preferably is conducted in buffer. The buffer is not specifically limited and can be, for example, Tris-HCl buffer, EPPS buffer, PIPES buffer, etc.

The FAOD treatment is conducted, for example, under the following conditions: the FAOD concentration in the reaction solution in the range of 0.1 to 10 KU/l, the temperature in the range of 15° C. to 50° C., the reaction time in the range of 1 to 60 minutes, and the pH in the range of 6 to 9; preferably, the FAOD concentration in the range of 0.5 to 2 KU/l, the temperature in the range of 30° C. to 37° C., the reaction time in the range of 5 to 20 minutes, and the pH in the range of 7 to 8.

Next, the hydrogen peroxide generated by the FAOD treatment is determined utilizing a redox reaction, by using the peroxidase (POD) and substrate that develops color by oxidization.

Generally, the redox reaction is induced in buffer under the conditions decided appropriately depending on the concentration of the hydrogen peroxide in the reaction solution, etc. For example, the redox reaction is induced under the following conditions: the POD concentration in the reaction solution in the range of 10 U/l to 400 KU/l, the reaction temperature in the range of 15° C. to 40° C., the reaction time in the range of 0.1 to 5 minutes, and the pH in the range of 5 to 10; more preferably, the POD concentration in the range of 50 U/l to 20 KU/l, the reaction temperature in the range of 30° C. to 37° C., the reaction time in the range of 0.1 to 1 minutes, and the pH in the range of 5 to 8. Furthermore, the buffer is not specifically limited and can be, for example, the same buffer as that used in the above-mentioned FAOD treatment.

In the case where the chromogenic substrate described above is used as the substrate, the concentration of the hydrogen peroxide can be determined by measuring the color development (i.e., absorbance of the reaction solution) with a spectrophotometer. From the concentration of the hydrogen peroxide, the concentration of the glycated protein in the sample can be determined.

In this determination process, the respective treatment steps may be performed individually as described above. In some cases, some of the steps or all of the steps may be performed simultaneously. For example, the α-GARE treatment step and the FAOD treatment step can be performed simultaneously by adding the α-GARE and FAOD to the sample at the same time to cause the reaction. Also, the FAOD treatment step and the color development step using POD can be performed simultaneously by adding FAOD, POD, and the chromogenic substrate to the degradation product obtained through the α-GARE treatment at the same time to cause the reaction. In addition, the step of inducing hemolysis by the surfactant and the α-GARE treatment step also can be perform simultaneously.

EXAMPLES

Example 1

In the present example, a glycated peptides having α-GA were reacted with a culture supernatant of a novel bacterial strain producing α-GARE according to the present invention to release the α-GA therefrom. Unless otherwise described, culture of the bacterial strain, degradation of the glycated peptides, and TLC analysis of the degradation products were conducted in the same manner as in the above-mentioned screening method.

First, the novel bacterial strains of the invention shown below respectively were inoculated into 5 ml of the liquid nutrient medium (pH 8.0), and then were cultured by a shake culture at 30° C. for 48 hours. The culture solutions thus obtained were centrifuged to remove the bacterial cells and the supernatants obtained were used as crude enzyme solutions.

(Bacterial Strains)

Sphingobacterium mizutae KDK1003 (FERM P-17348)
Sphingomonas parapaucimobilis KDK1004 (FERM BP-7041)
Comamonas acidovorans KDK1005 (FERM P-17346)
Mucor circinelloides f. janssenii KDK3004 (FERM P-17345)
Penicillium waksmanii KDK3005 (FERM P-17344)

Figure 1:
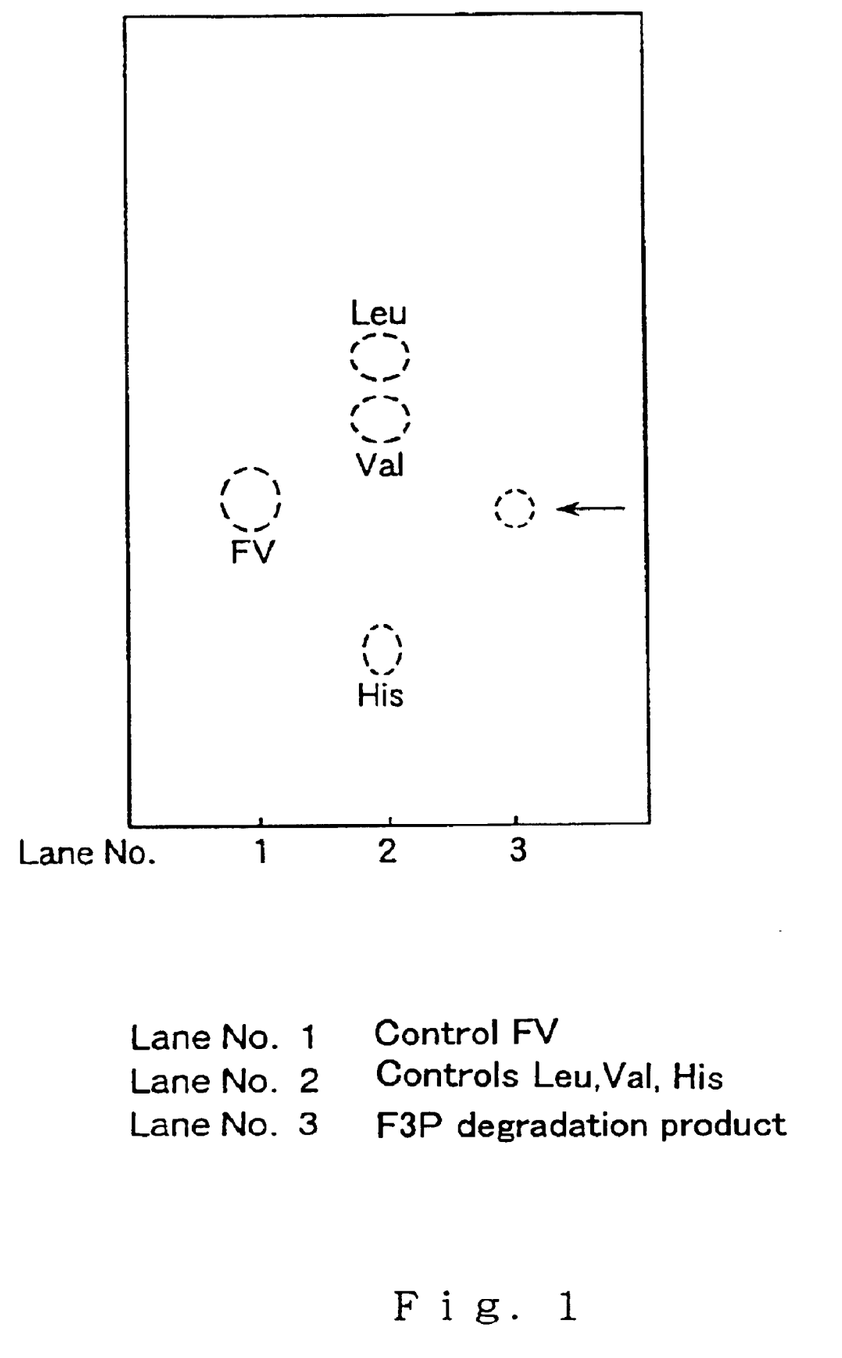
FIG. 1 is a chromatogram resulting from TLC analysis for degradation products obtained by degrading glycated peptides with a culture supernatant of a bacterial strain of the genus *Sphingobacterium* in an example of the present invention.
Figure 2:
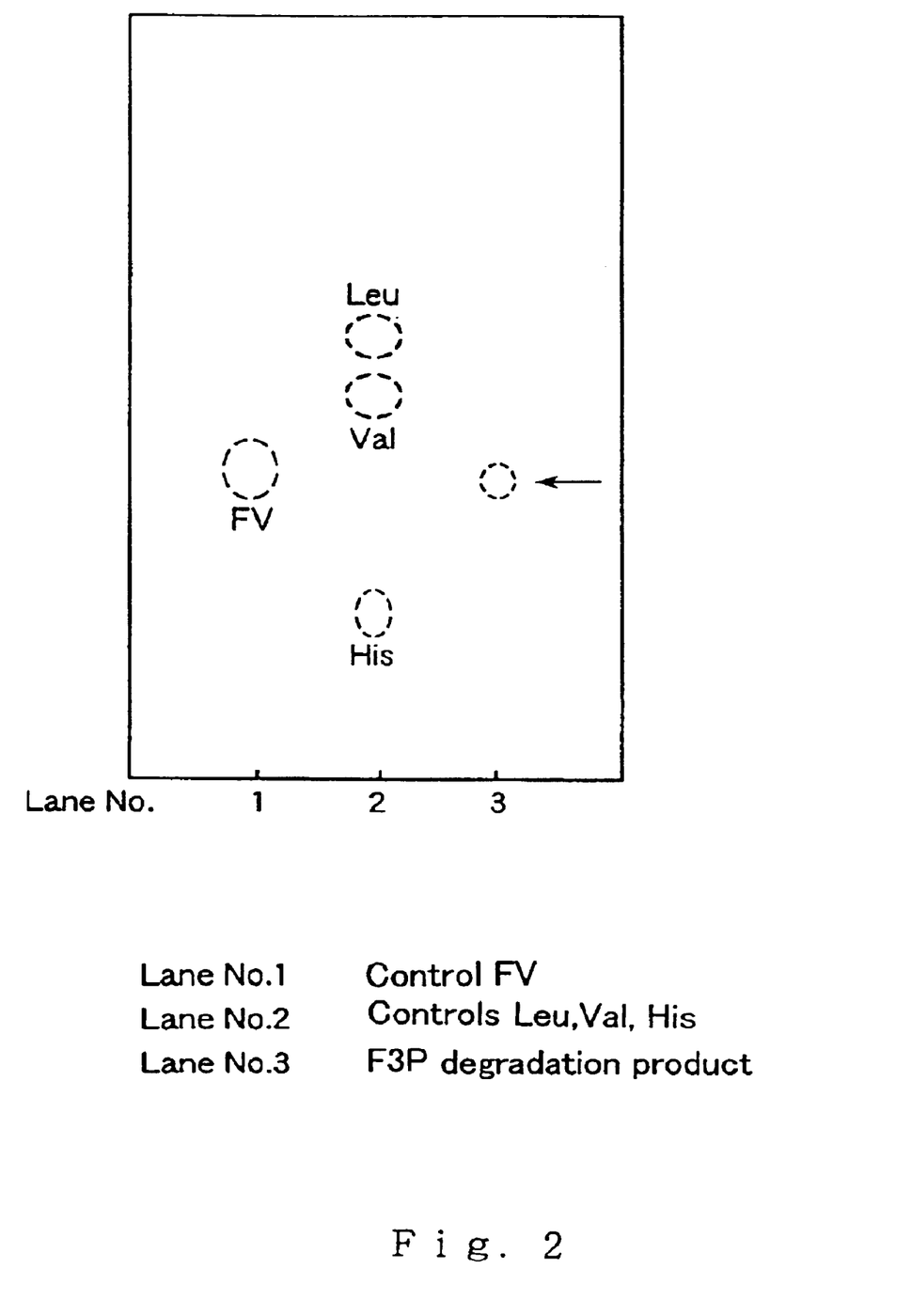
FIG. 2 is another chromatogram resulting from TLC analysis for degradation products obtained by degrading glycated peptides with a culture supernatant of a bacterial strain of the genus *Sphingomonas* in the same example.
Figure 3:
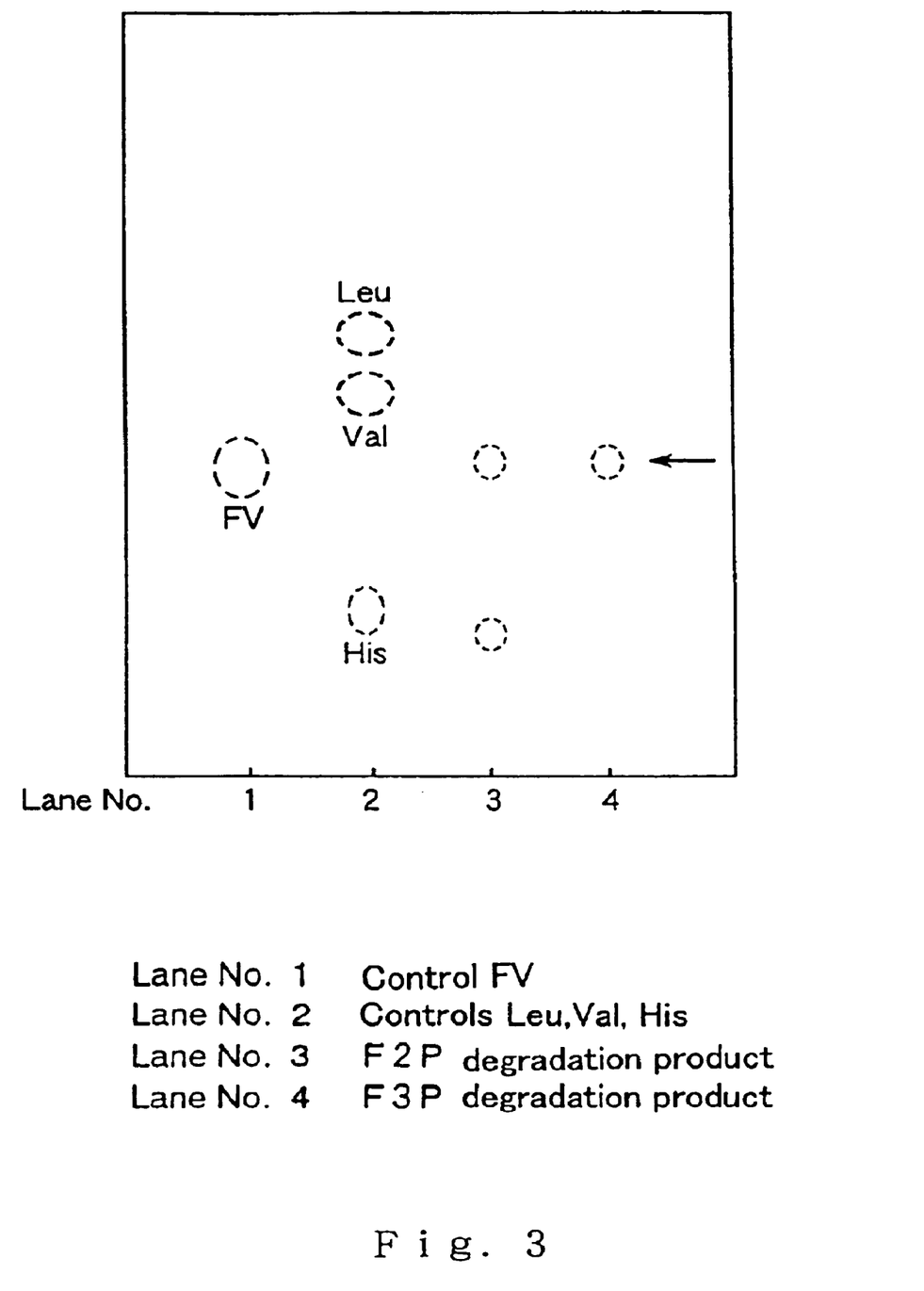
FIG. 3 is a chromatogram resulting from TLC analysis for degradation products obtained by degrading glycated peptides with a culture supernatant of a bacterial strain of the genus *Comamonas* in another example of the present invention.
Figure 4:
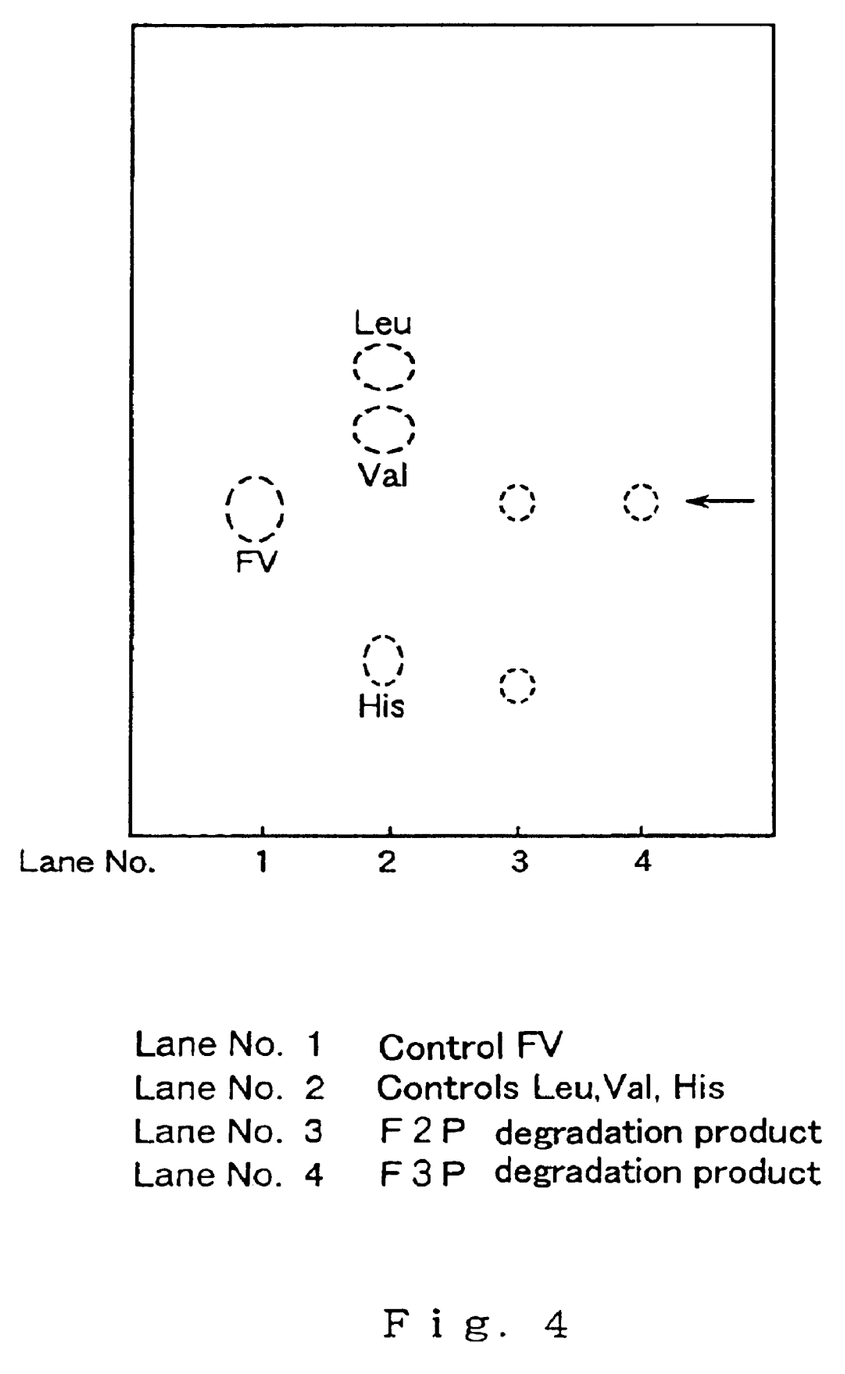
FIG. 4 is another chromatogram resulting from TLC analysis for degradation products obtained by degrading glycated peptides with a culture supernatant of a bacterial strain of the genus *Mucor* in the same example.
Figure 5:
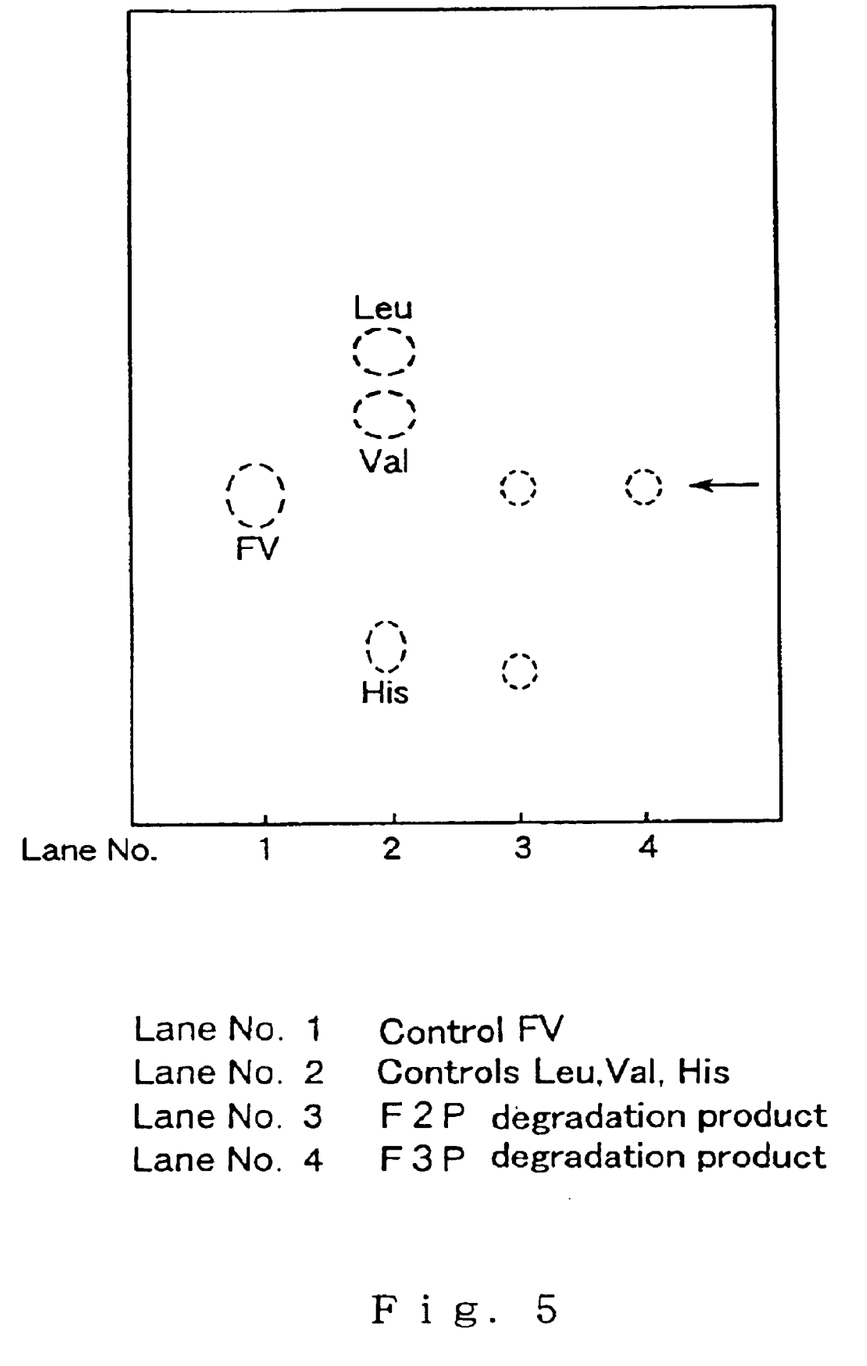
FIG. 5 is a chromatogram resulting from TLC analysis for degradation products obtained by degrading glycated peptides with a culture supernatant of a bacterial strain of the genus *Penicillium* in another example of the present invention.

Next, 100 µl of each above-mentioned crude enzyme solution was mixed with 50 µl of the above-mentioned 0.01 mol/l aqueous solutions of the glycated peptides (F2P and F3P), respectively. The resultant mixtures were reacted at 30° C. overnight, and the reaction solutions thus obtained were analyzed by TLC. The results of this TLC analysis are shown in FIGS. 1 to 5. FIGS. 1 to 5 are chromatograms resulting from TLC analysis with respect to Sphingobacterium mizutae KDK1003 (FERM P-17348), Sphingomonas parapaucimobilis KDK1004 (FERM BP-7041), Comamonas acidovorans KDK1005 (FERM P-17346), Mucor circinelloides f. janssenii KDK3004 (FERM P-17345), and Penicillium waksmanii KDK3005 (FERM P-17344), respectively. In FIG. 1, Lane No. 1 shows a control (FV) and Lane No. 2 shows other controls (Leu, Val, His). In FIGS. 1 and 2, Lane No. 3 shows the F3P degradation product. In FIGS. 3 to 5, Lane No. 3 shows the F2P degradation product and Lane No. 4 shows the F3P degradation product. Further, mobility of the spots marked with the arrows in these drawings are shown in Table 1 below.

TABLE 1

| FIG. No. | Samples | Mobility |
|---|---|---|
| FIG. 1 | Control FV | 0.43 |
|  | F3P degradation product | 0.44 |
| FIG. 2 | Control FV | 0.43 |
|  | F3P degradation product | 0.44 |
| FIG. 3 | Control FV | 0.40 |
|  | F2P degradation product | 0.42 |
|  | F3P degradation product | 0.40 |
| FIG. 4 | Control FV | 0.40 |
|  | F2P degradation product | 0.40 |
|  | F3P degradation product | 0.42 |
| FIG. 5 | Control FV | 0.40 |
|  | F2P degradation product | 0.40 |
|  | F3P degradation product | 0.42 |

As shown in FIGS. 1 to 5 and Table 1 above, the degradation products of the glycated peptides treated with the respective crude enzyme solutions were seen as the spots (marked with the arrows in the drawings) with the same mobility as that of the spot of the control FV. These results demonstrate that α-GARE according to the present invention releases α-GA from a glycated peptide. Further, since the spots of the above degradation products had the different mobility than that of Val, it was found that the sugar was not dissociated from FV released by α-GARE. In addition, as shown in FIGS. 3 to 5, the F2P degradation product exhibited the spots of FV and His. The reason why the F3P degradation product and F5P degradation product did not exhibit the spots of degradation products other than FV (dipeptide) is considered that they are hardly detect by this TLC method.

Example 2

In the present example, release of α-GA (FV) was confirmed in a glycated peptide that has been treated with a crude enzyme derived from a novel bacterial strain according to the present invention.

Sphingomonas parapaucimobilis KDK1004 (FERM BP-7041) was cultured by a reciprocal shake culture in the above-mentioned Hb culture medium (pH 6.0) at 28° C. for 5 days. Then, the resultant culture solution was centrifuged (12,000 G, 15 min, 4° C.), and the supernatant obtained was used as a crude enzyme solution.

To 50 µl of 0.01 mol/l F4P aqueous solution were added 100 µl of the crude enzyme solution and 50 µl of 0.2 mol/l potassium phosphate buffer (pH 8.0), and the resultant mixture was reacted at 37° C. overnight. The reaction solution thus obtained was applied to an ultrafiltration membrane (5 kDa molecular weight cut off: the trade name "Ultra Free MC Filter" available from Millipore Corporation, hereinafter the same) to remove high molecular substances such as proteins or the like. The solution thus obtained was then lyophilized.

Next, the lyophilized product was dissolved in 20 µl of the eluent A shown below. The resultant solution was subjected to reverse phase chromatography under the conditions shown below and the solution was fractionated every 15 seconds (250 µl/1 fraction) after the start of the analysis. Further, FV as a control was eluted under the same conditions and the elution time thereof was measured.

(Reverse Phase Chromatography)

| Column; | Trade name "Hypercarb" (GL Sciences Inc.) |
|---|---|
| Size; | 100 mm × 4.6 mm |
| Loop; | 1000 µl |
| Eluent A; | trifluoroacetic acid:distilled water = 0.1:100 (volume ratio) |
| Eluent B; | trifluoroacetic acid:distilled water:acetonitrile = 0.1:80:20 (volume ratio) |
| Gradient conditions; | 0 to 25 minutes: 0 to 20 vol. % eluent B after 25 minutes: 20 vol. % eluent B |
| Flow rate; | 1 ml/min |
| Column temperature; | 37° C. |
| Detection wavelength; | 210 nm, 230 nm |

Subsequently, with respect to each separation fraction obtained through the above-mentioned reverse phase chromatography, detection of FV was conducted in the manner described below.

(Detection Method for FV)

First, 20 µl of a 10 µmol/l hydrogen peroxide aqueous solution was added to 20 µl of the respective separation fraction solutions. Then, 60 µl of the redox solution A shown below was further added and the resultant mixtures were reacted at 37° C. for 15 minutes. Next, the absorbance of these reaction solutions at the main wavelength of 694 nm and the sub-wavelength of 884 nm was measured by means of a biochemical automatic analysis apparatus (the trade name "JCA-BM 8" available from Japan Electron Optics Laboratory Co. Ltd., hereinafter the same).

(Composition of Redox Solution A)

| Trade name "DA 64" (Wako Pure Chemical Industries, Ltd., hereinafter the same) | 33 µmol/l |
|---|---|
| POD (Type III: Toyobo Co., Ltd., hereafter the same) | 33 KU/l |
| FAOD (Asahi Chemical Industry Co., Ltd.) | 3.3 KU/l |
| Potassium phosphate buffer (pH 8.0) | 0.17 mol/l |

As a result, color development was observed in the separation fractions corresponding to the elution time of 5 to 6 minutes in the reverse phase chromatography. Such elution time was equivalent to that of the control FV and thus suggested that FV was present in the F4P degradation product.

Example 3

In the present example, an α-GARE activity was confirmed at various α-GARE concentrations.

(1) Preparation of Partially Purified Enzyme

*Sphingomonas parapaucimobilis* KDK1004 (FERM BP-7041) was cultured in the same manner as in Example 2. Supernatant was collected from the culture solution and used as a crude enzyme solution. Then, 50 ml of the crude enzyme solution was concentrated so as to give a final volume of 5 ml using the ultrafiltration membrane (5 kDa molecular weight cut off), and then was partially purified by gel chromatography conducted under the following conditions.

| (Gel Column Chromatography) | |
| --- | --- |
| Column: | Trade name "Superdex 200 pg" (Pharmacia Corporation) |
| Column size: | inside diameter = 260 mm, length = 600 mm |
| Flow rate; | 5.2 ml/min |
| Detection wavelength; | 280 nm, 230 nm |
| Eluent: | 20 mol/l potassium phosphate buffer (pH 7.5) |
| 1 fraction: | 7 ml |

(2) Determination of α-GARE Activity (Degradation Method)

Predetermined amounts (25, 50, 75, 100, 125, and 140 μl) of the above-mentioned partially purified α-GARE and 1 mol/l potassium phosphate buffer (pH 8.0) were added to 50 μl of 10 mol/l F3P aqueous solutions, respectively, and the resultant mixtures were reacted at 37° C. overnight. The total volume of the reaction solution was set to 200 μl so that the above buffer was contained in the solution at the final concentration of 50 mmol/l.

(Determination Method)

Figure 6:
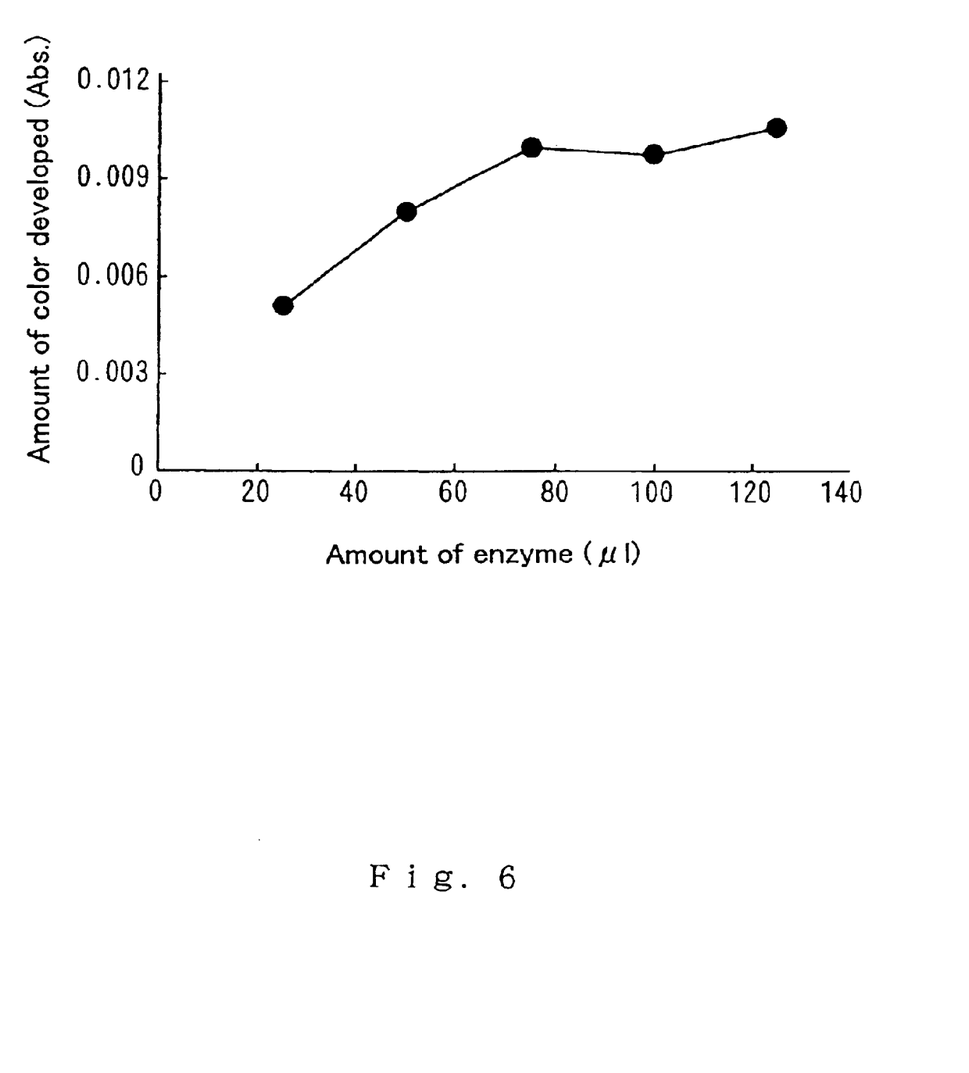
FIG. 6 is a graph showing the relationship between the amount of α-GARE derived from a bacterial strain of the genus *Sphingomonas* and the absorbance in still another example of the present invention.

The reaction solution was diluted 3-fold (by volume) with distilled water. To 25 μl of this dilute solution were added 15 μl of 10 mol/l hydrogen peroxide solution and 70 ml of the following redox solution B in this order, and the result mixture was reacted at 37° C. for 15 minutes. Subsequently, according to the same manner as in Example 2, the absorbance of the mixture was measured. Then, using the value obtained in the absence of each α-GARE as a blank, an increase in the absorbance per 5 minutes was determined as an α-GARE activity. The results are shown in FIG. 6. FIG. 6 is a graph showing the relationship between the amount of the α-GARE derived from *Sphingomonas parapaucimobilis* KDK1004 (FERM BP-7041) and the amount of the color developed (absorbance).

| (Composition of Redox Solution B) | |
| --- | --- |
| "DA 64" | 31 μmol/l |
| POD | 31 KU/l |
| FAOD | 0.8 KU/l |
| Potassium phosphate buffer (pH 8.0) | 0.16 mol/l |

As shown in FIG. 6, the activity of the α-GARE increased in an amount-dependent manner when the amount of the α-GARE is in the range of 20 to 100 μl.

Example 4

In the present example, thermal stability of α-GARE according to the present invention was confirmed.

Figure 7:
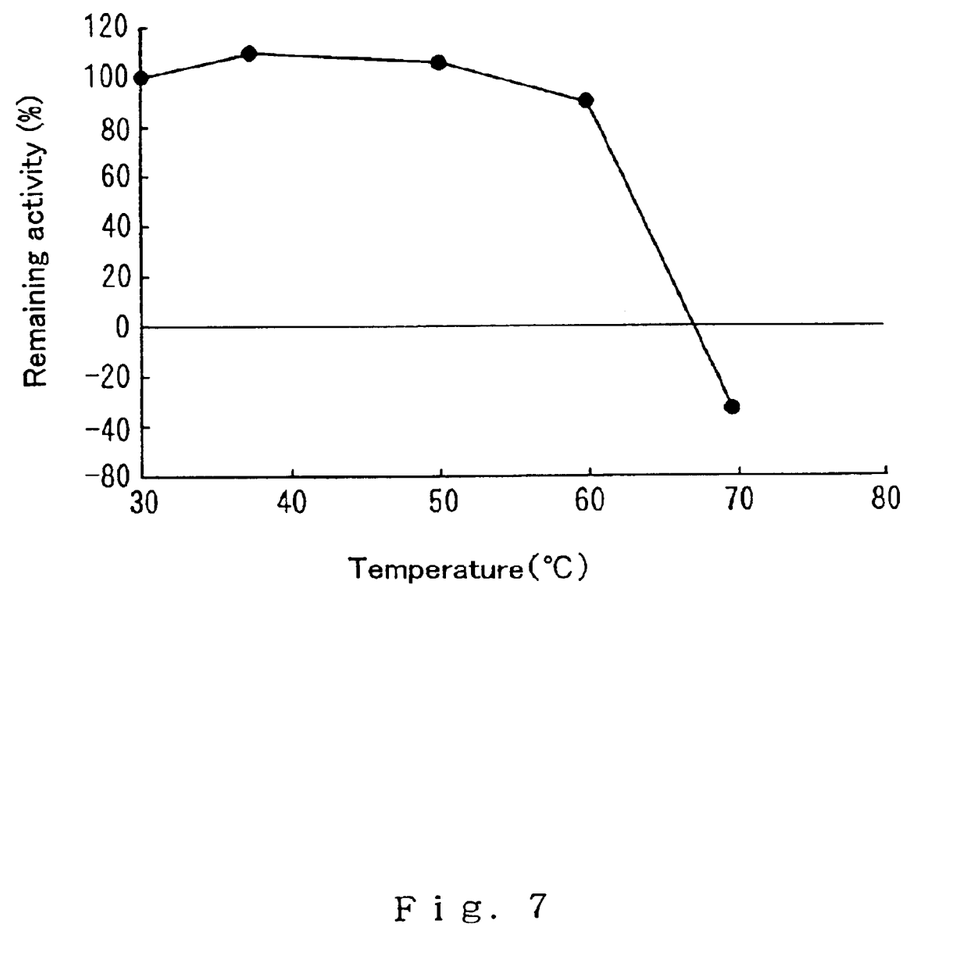
FIG. 7 is a graph showing thermal stability of α-GARE derived from a bacterial strain of the genus *Sphingomonas* in still another example of the present invention.

The partially purified enzyme prepared from the α-GARE derived from *Sphingomonas parapaucimobilis* KDK1004 (FERM BP-7041) in Example 3 were incubated at respective temperatures (30° C., 37° C., 50° C., 60° C., and 70° C.) for 20 minutes. To 50 μl of the same F3P aqueous solution as that used in Example 3 were added 100 μl of the heat-treated partially purified enzymes and 50 μl of 50 mol/l potassium phosphate buffer (pH 8.0), and the resultant mixtures were reacted at 37° C. for 18 hours. Subsequently, according to the same manner as in Example 3, a redox reaction was induced to in 20 μl of the resultant reaction solutions by the use of FAOD and the absorbance of each solution was measured. An increase in the absorbance per 5 minutes was determined as an α-GARE activity and, letting the activity of the non-heat-treated α-GARE be 100%, a remaining activity (%) was calculated. The results are shown in FIG. 7. FIG. 7 is a graph showing the thermal stability of the α-GARE derived from *Sphingomonas parapaucimobilis* KDK1004 (FERM BP-7041).

As shown in FIG. 7, the α-GARE exhibited a remaining activity of 100% even after the heat treatment at 30° C. to 50° C. However, the α-GARE was inactivated completely by the heat treatment at 70° C.

Example 5

In the present example, an optimum temperature of α-GARE according to the present invention was confirmed.

Figure 8:
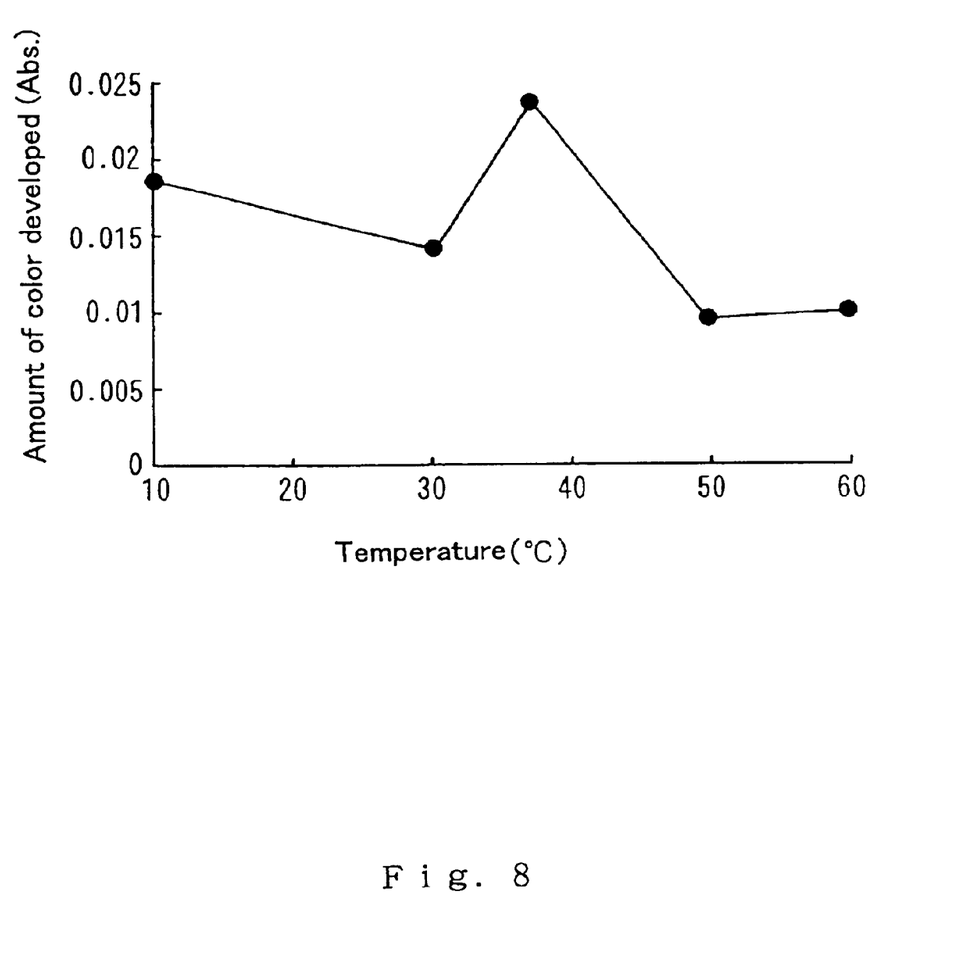
FIG. 8 is a graph showing an optimum temperature of α-GARE derived from a bacterial strain of the genus *Sphingomonas* in still another example of the present invention.

To 50 μl of the same F3P aqueous solution as used in Example 3 were added the partially purified enzyme prepared from the α-GARE derived from *Sphingomonas parapaucimobilis* KDK1004 (FERM BP-7041) in Example 3 and 50 μl of 50 mol/l potassium phosphate buffer (pH 8.0). The resultant mixture was reacted at respective temperatures (10, 30° C., 37° C., 50° C., 60° C., and 70° C.) for 8 hours. The reaction solutions were diluted 3-fold with distilled water. With respect to 25 μl of dilute solutions, a redox reaction was induced by the use of FAOD and the absorbance of each solution was measured according to the same manner as in Example 3. Then, an increase in the absorbance per 5 minutes was determined as an α-GARE activity. The results are shown in FIG. 8. FIG. 8 is a graph showing an optimum temperature of the α-GARE derived from *Sphingomonas parapaucimobilis* KDK1004 (FERM BP-7041).

As shown in the drawing, the optimum temperature of the α-GARE was in the vicinity of 37° C.

Example 7

In the present example, a molecular weigh of α-GARE according to the present invention was confirmed.

According to the same manner as in Example 3, the culture supernatant of *Sphingomonas parapaucimobilis* KDK1004 (FERM BP-7041) was separated through gel chromatography conducted under the same conditions. Subsequently, according to the same manner as in Example 3, a redox reaction was induced in each fraction by the use of FAOD to determine an α-GARE activity. On the other hand, a molecular weight marker (the trade name "MW Marker (HPLC)" available from Oriental Yeast Co., Ltd.) was applied to the gel column chromatography conducted under the same condition. From the calibration curve of the molecular weight obtained from the gel column chromatography and the result of the α-GARE elution, it was assumed that the molecular weight of the α-GARE derived from *Sphingomonas parapaucimobilis* KDK1004 (FERM BP-7041) was about 40,000 to 50,000.

INDUSTRIAL APPLICABILITY

As specifically described above, a novel enzyme, α-GARE, according to the present invention can release an amino acid residue having a glycated α-amino group from a glycated protein etc. Accordingly, if α-GARE is used in a method of determining the glycated protein etc. using FAOD, HbA1c as an index for diabetes can be determined accurately and easily. Therefore, the determination of HbA1c can be made practice in clinical tests etc.

What is claimed is:

1. An isolated enzyme that releases an amino acid having a glycated α-amino group from a glycated protein or a glycated peptide, which is derived from bacterial strain *Sphingobacterium mizutae* KDK1003 (FERM P-17348).

2. An enzyme according to claim 1, wherein the amino acid having a glycated α-amino group to be released is valine having a glycated α-amino group.

* * * * *